United States Patent [19]

Wilson

[11] Patent Number: 5,501,225
[45] Date of Patent: Mar. 26, 1996

[54] IMAGING OF TISSUE OXYGEN USING NEEDLE PHOSPHORIMETER

[76] Inventor: David F. Wilson, 207 St. Marks Sq., Philadelphia, Pa. 19104

[21] Appl. No.: 22,190

[22] Filed: Feb. 25, 1993

Related U.S. Application Data

[63] Continuation-in-part of Ser. No. 763,184, Sep. 20, 1991, Pat. No. 5,279,297.

[51] Int. Cl.$^6$ .................................................. G01N 21/64
[52] U.S. Cl. ............................................................ 128/665
[58] Field of Search .................................. 128/633, 634, 128/664, 665, 653.1

[56] References Cited

U.S. PATENT DOCUMENTS

| | | | |
|---|---|---|---|
| 4,752,115 | 6/1988 | Murray, Jr. et al. | 128/634 |
| 4,833,091 | 5/1989 | Leader et al. | 128/634 |
| 4,898,175 | 2/1990 | Noguchi | 128/634 |
| 4,906,249 | 3/1990 | Fogt et al. | 128/634 |
| 4,947,850 | 8/1990 | Vanderkool et al. | |
| 5,012,809 | 5/1991 | Shulze | 128/634 |
| 5,043,286 | 8/1991 | Khalil et al. | 128/634 |
| 5,127,405 | 7/1992 | Alcala et al. | 128/634 |

*Primary Examiner*—William E. Kamm
*Assistant Examiner*—Marianne Parker
*Attorney, Agent, or Firm*—Duane, Morris & Heckscher

[57] ABSTRACT

A method for producing a detecting phosphorescent emission from a body portion comprising the following steps: inserting phosphorescent material into the body portion; inserting a needle into said body portion, said needle encasing a light guide for propagating a light signal therethrough, said light signal exciting said phosphorescent material within said body portion so as to produce a phosphorescent emission having a radius of visibility; and collecting the phosphorescent emission using a collector placed proximate to the surface of the body portion. The present invention also encompasses apparatus for inserting an excitation light into a tissue sample comprising: a needle having a light guide extending axially within the needle, the light guide being configured to transmit an excitation light into the body portion, so as to a phosphorescent carrier medium within the tissue sample.

10 Claims, 3 Drawing Sheets

IMAGING OF TISSUE OXYGEN USING NEEDLE PHOSPHORIMETER

RELATED CASES AND CLAIM OF PRIORITY

This case is a continuation-in-part of U.S. Ser. No. 07/763,184, filed Sep. 20, 1991, entitled METHOD AND APPARATUS FOR OXYGEN MAPPING now U.S. Pat. No. 5,279,297.

FIELD OF THE INVENTION

The present invention generally relates to the imaging of the body portions of animals, and specifically to the field of phosphorimetry.

BACKGROUND OF THE INVENTION

The present invention is based upon the observation that oxygen can have a quenching effect on the molecular luminescence of various chemical compounds and that this effect may be employed for imaging oxygen concentrations of the body portions of animals. Information about the distribution and concentration of oxygen is extremely useful in that it is indicative of tissue structure, anomalies, defects and diseases. The reader is referred to the above-cited U.S. Pat. No. 4,947,850 for further discussion of the Background of the present invention.

Co-pending U.S. Ser. No. 07/763,184, filed Sep. 20, 1991, entitled Method and Apparatus for Oxygen Mapping discloses improved methods and apparatus for imaging internal body structures of animals. The apparatus and methods disclosed in this application are directed to imaging system in which light focussed through an epifluorescence attachment excites a phosphorescent material within a body portion or tissue. The light emanating from the phosphorescent material is then collected from outside of the tissue.

While the embodiments disclosed in co-pending application Ser. No. 07/763,184 disclose a system for detecting oxygen pressure levels, they do not disclose a device which can be used to isolate and measure the oxygen pressure of specific sections of back/portion or tissue sample. It would be desirable to provide an apparatus and method which could make precise measurements of oxygen pressure. It would further be desirable to provide a device and method which can more precisely control the input of light to tissue or body portions examination when making oxygen pressure determinations.

SUMMARY OF THE INVENTION

In accordance with the above needs, the present invention provides improved methods and apparatus for imaging internal body structures of animals. The methods and apparatus of the present invention provide numerous advantages over prior art systems. In a preferred embodiment, the present invention is directed to a method for producing a phosphorescent emission within a body portion comprising the following steps: inserting a phosphorescent probe material into the body portion; and inserting a needle into said body portion, said needle supporting a light guide for propagating a light signal having a first wavelength into said body portion, said light signal exciting said phosphorescent probe material within said body portion, thus producing an emission of phosphorescent light having a radius of visibility.

In a more preferred embodiment, the present invention is directed to a method for producing a phosphorescent emission from a body portion comprising the following steps: inserting a phosphorescent material into the body portion; inserting a needle into said body portion, said needle encasing a light guide extending axially through said needle for propagating a light signal through said needle, said light signal exciting said phosphorescent material within said body portion, thus producing the emission of a phosphorescent light signal; and collecting said phosphorescent emission using a collector system placed proximate to the surface of said body portion.

In additional embodiments, the present invention is directed to a method for determining the oxygen pressure of a body portion comprising the following steps: inserting a phosphorescent material into the body portion; inserting a needle into said body portion, said needle encasing a light guide extending axially through said needle; propagating a light signal through said light guide and into said body portion, said light signal exciting said phosphorescent material within said body portion, thus producing the emission of a phosphorescent light signal having a radius of emission, the duration of said emission being proportional to the oxygen pressure of said body portion; and collecting said phosphorescent emission using a collector system placed proximate to the surface of said body portion.

The present invention further discloses a method for determining the oxygen pressure of at least two points of a body portion comprising the following steps: inserting a phosphorescent material into the body portion; inserting a needle into said body portion to a first point in said body portion, said needle encasing a light guide extending axially through said needle; propagating a light signal through said light guide and into said body portion at said first point, said light signal exciting said phosphorescent material within said body portion at said first point, thus producing the emission of a phosphorescent light signal having a radius of emission, the duration of said emission being proportional to the oxygen pressure of said first point; capturing said phosphorescent emission using a collector lens placed proximate to the surface of said body portion; moving said needle to a second point in said body portion; propagating a light signal through said light guide and into said body portion at said second point, said light signal exciting said phosphorescent material within said body portion at said second point, thus producing the emission of a second phosphorescent light signal, the duration of said emission being proportional to the oxygen pressure at said second point; and collecting said second phosphorescent emission using a collector lens placed proximate to the surface of said body portion.

The present invention is further directed to apparatus for inserting an excitation light into a body portion containing a phosphorescent medium comprising: a needle having an axial passageway for insertion into the body portion; a light guide extending through said axial passageway, said light guide transmitting an excitation light signal through said needle and into said body portion such that when light guide transmits said excitation light signal through said light guide, the phosphorescent medium within said body portion is excited.

Other features and advantages of the invention are described below in connection with the detailed description of preferred embodiments.

DETAILED DESCRIPTION OF PREFERRED EMBODIMENTS

Figure 1:
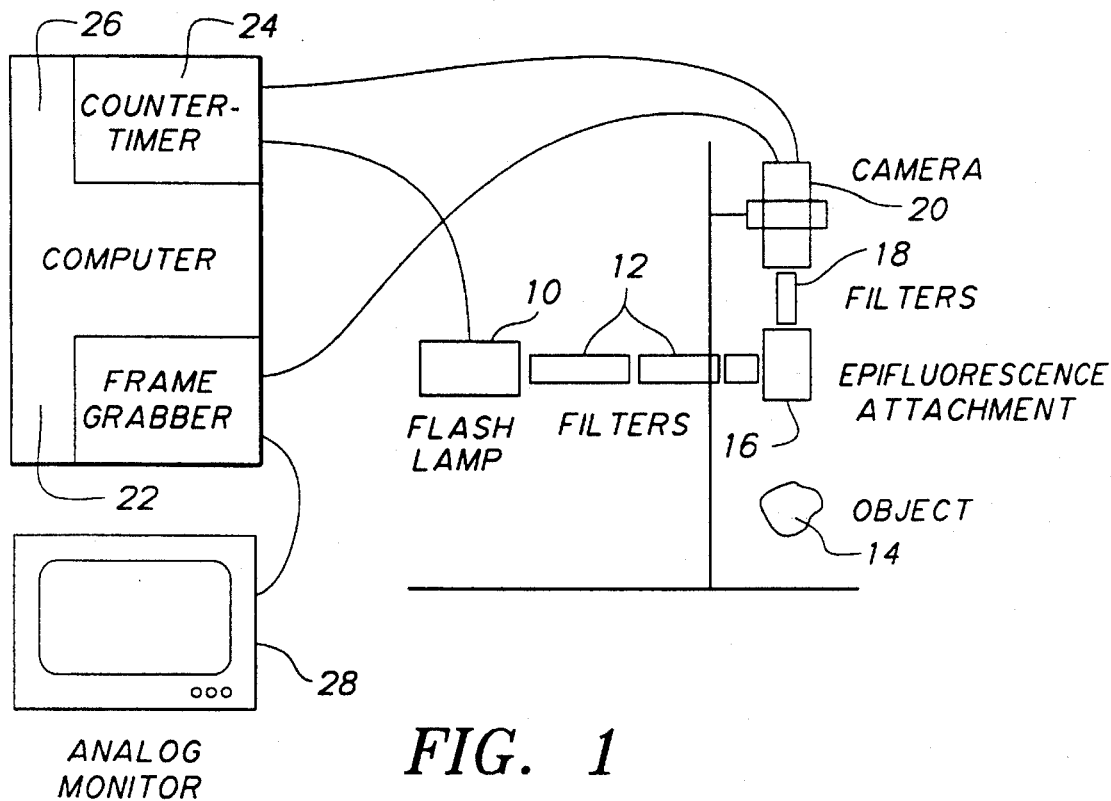
FIG. 1 is a block diagram of one embodiment of an imaging system.

Referring to FIG. 1, a measurement system in accordance with the present invention includes an illuminating light source 10, optical filter(s) 12, a microscope and an associated epifluorescence attachment 16, a long pass cutoff filter 18, a camera 20, a frame grabber 22, a counter timer board 24, a computer 26 and an analog monitor 28. The frame grabber 22 and counter timer board 24 are mounted in the computer 26. In one preferred embodiment the illuminating light source 10 is an EG&G flash lamp with a flash duration of less than 5 us; the microscope is a Wild-Leitz Macrozoom microscope; the long pass cutoff filter 18 provides 50% transmission at 630 nm; the camera 20 is a Xybion intensified (gain approximately 18,000) CCD camera with a red sensitive coating on the intensifier and capable of capturing 30 frames per second in its diode storage array;the frame grabber 22 is a Matrox MVP-AT frame grabber; the counter time board 24 is a CTM-05 board (available from MetraByte Corp., Taunton, Mass.); and the computer 26 is an IBM-PC/AT compatible 80386/16 MHZ computer.

According to the present invention, the light from the flash lamp 10 is passed through the optical filters 12, to remove an unwanted portion of the spectrum, and focused on a sample object 14 through the epifluorescence attachment 16; phosphorescence is then observed through the long pass cutoff filter 18. The images are collected with the camera 20 and the frame grabber 22 is used to digitize and average frames while the timing of the flash and gating of the camera intensifier is controlled by the counter timer board 24. The computer 26, operating under the direction of software (not shown) in accordance with the present invention, controls the counter timer board 24, camera intensifier, frame grabber 22 and a computer storage device (not shown). A concise description of a preferred method of operation is provided below with reference to the flowchart of FIG. 2.

The following list briefly enumerates the basic processes or steps of method for operating the imaging system of FIG. 1 to obtain an oxygen map of a body portion (labelled "object" in FIG. 1) of a subject:

1. Collection of the image of phosphorescence for a given period of time after illumination with the flash lamp.
   a) Preparation of the camera 20 (including clearing of the camera storage array and suppression of the image output).
   b) Firing of the flash lamp 10.
   c) Setting the delay and gating of the camera intensifier (i.e., setting duration of delay and duration the intensifier is on).
   (d) Triggering transfer of the image to the frame grabber 22. This sequence is repeated as many times as the operator requests, typically from 2 to 32 times. The images are averaged in real time.
   (e) Transfer of the averaged image to a computer storage device.

2. Display of the phosphorescence intensity images during the above experimental protocol.

The image is displayed on a monitor for observation by the operator at the end of collection of the average phosphorescence intensity image for each delay time. Each image is displayed until the next image has been collected.

3. Collection of the sequence of images with different delay times after the flash.

The steps of paragraph 1 (or process)above are repeated with the counter-timer board 24 programmed for different delays after the flash according to the sequence requested by the operator. The result is a series of images stored on the computer storage device, each for a different delay time after the flash. A typical sequence of images might consist of delays after the flash of 20 μs, 40 μs, 80 μs, 160 μs, 300 μs, 300 μs and 2,500 μs, each with a gate width (period of time the intensifier is on) of 2,500 μs.

4Analysis of the data:

The images are placed in a computer memory and each is smoothed with a filter to reduce any noise.

b) The background intensity image is subtracted from all the other images. The background is an image collected with a delay of more than 5 times the phosphorescence lifetime, when the phosphorescence lifetime, when the phosphorescence emission is negligible in comparison to the emissions corresponding to the delay periods of interest (e.g., a delay of 2,500 μs may be used as a background when the lifetimes expected to be measured are from 60 to 600 μs).

c) The phosphorescence lifetimes are calculated for each pixel of the image array by a linear regression best fit to a single exponential (i.e.,the parameters of an exponentially decaying function or curve are derived). This facilitates the generation of two new two-dimensional maps, one of the initial (zero delay) phosphorescence intensities and one of the phosphorescence lifetimes. The correlation coefficient for the fit of the data to the single exponential is calculated for each lifetime and these are stored as an additional two-dimensional map. Routines for fitting to multiexponential decay may also be included.

d) The oxygen pressure map is calculated from the phosphorescence lifetime map and the values for $kg_q$ and $T_o$ (determined independently in calibration experiments) using the Stern-Volmer relationship:

$$T_o/T = 1 + k_q * T_o * po2'$$

where $T_o$ (also called "τo") represents the lifetime in the absence of oxygen, $k_q$ represents the quenching constant for oxygen and $po_2$ represents the oxygen pressure for a lifetime of T. It is apparent that the above relationship holds whether po2 represents oxygen pressure or oxygen concentration, as each one of those parameters is proportional to the other.

5. Processing of the phosphorescence intensity data:

Data processing software written in C language using the Watcom C Professional version 8.0, 332 bit, 386 protected mode compiler (available from Watcom Systems, Inc., Waterloo, Ontario, Canada). To operate on large amounts of data, the C language program works under an OS/386 Developers kit version 2.1.05 DOS extender operating system (available from ERGO Computing Inc., Peabody, Mass.). The phosphorescence lifetimes and the correlation coefficients are calculated using least squares linear regression. There are additional image processing options designed to optimize the data presentation, including filters for smoothing and edge enhancement, various graphical display options, and pseudocolor. The phosphorescence images and two-dimensional maps are displayed and/or hardcopied by a printer, in accordance with the operator's wishes.

Figure 2:
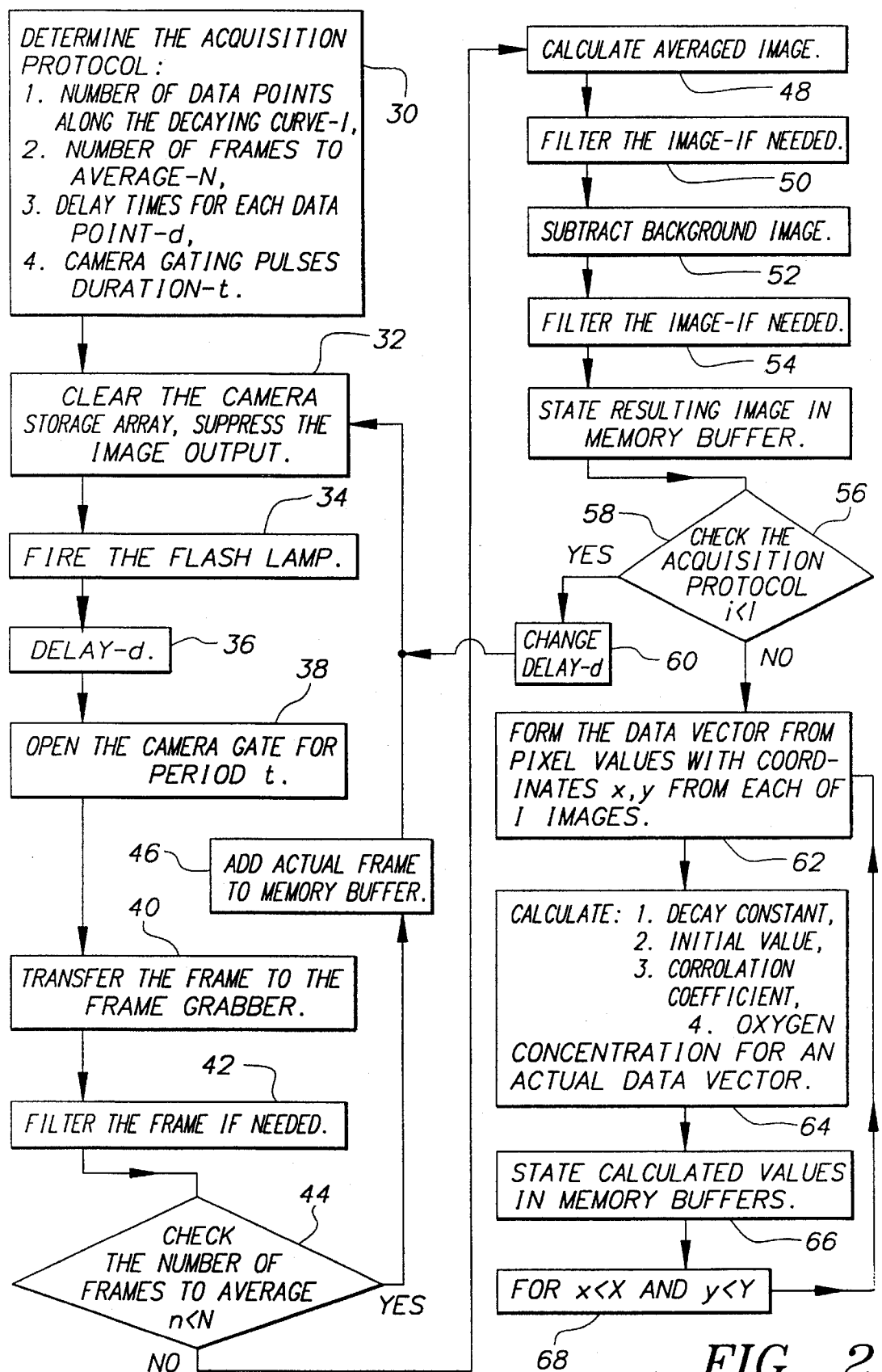
FIG. 2 is a flowchart of one method for oxygen mapping or imaging in accordance with the present invention.

Referring now to the flowchart of FIG. 2, the imaging system of FIG. 1 may be programmed in accordance with the present invention to perform the processes indicated in the respective blocks.

First, as shown in block 30, the computer determines the desired acquisition protocol. That process includes determining the desired number of data points (I) along each decaying luminescence curve (i.e., the number of images to collect), determining the number of frames (N) to average for each image, determining the delay period (d) and determining the duration (t) of each camera gating pulse.

The camera storage array is then cleared and the image output is suppressed (block 32). Next the flashlamp is fired (block 34). The system then waits for the prescribed delay period d (block 36). Next the camera gate is opened for the prescribed period t (block 38). A frame of data is then transferred from the camera to the frame grabber (block 40). Then, if necessary, the captured data frame is filtered (block 42).

At decision block 44 the computer determines whether the number of frames captured (n), which is one after the first pass through the loop, is less than N (the specified number of frames to average). If n is less than N, the program adds the captured frame to a memory buffer associated with the computer and then loops to block 32. If n is equal to or greater than N a composite frame is constructed from an average of corresponding pixels of the N captured frames (block 48). If necessary, the composite frame is filtered to remove noise or otherwise improve the quality of the data (block 50). At block 52 the previously-obtained background data is subtracted from the composite image. The resulting frame after subtraction of the background frame is then filtered as before if necessary (block 54) and stored in memory (block 56). The computer then determines whether the number of data points collected (i) is less than the prescribed number of points (or images) I (block 58). The program then changes the delay d (e.g., from 20 µs to 40 µs, from 40 µs to 80 µs, etc.) (block 60) and loops to block 32 if i is less than I; otherwise it proceeds to block 62 and forms data vectors corresponding to the pixels of the I frames of data with indices x, y.

At block 64 the computer calculates decay constants $T_{(x,y)}$ initial values $T_{o(x,Y)}$, and oxygen pressure or concentration values $pO_{2(x,y)}$ for that data vector. The calculated values are then stored in memory (block 66). At block 68 the computer determines whether x and y are less than their respective predefined maximum values (X, Y) and, if so, loops to block 62 to process the remaining pixels. Once the pressure map is obtained a representative image may be displayed using conventional image processing methods. That image may be advantageously employed in the detection of tissue anomalies, defects and diseases.

Figure 3:
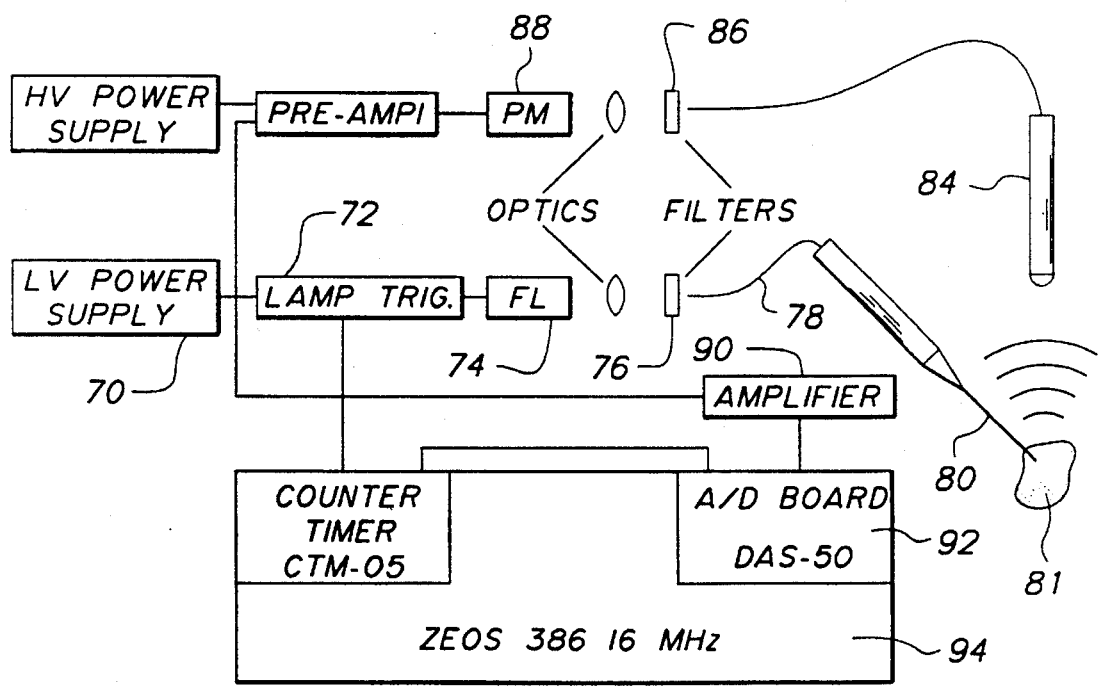
FIG. 3 is a block diagram of a of filtering system in accordance with an embodiment the present invention.
Figure 4:
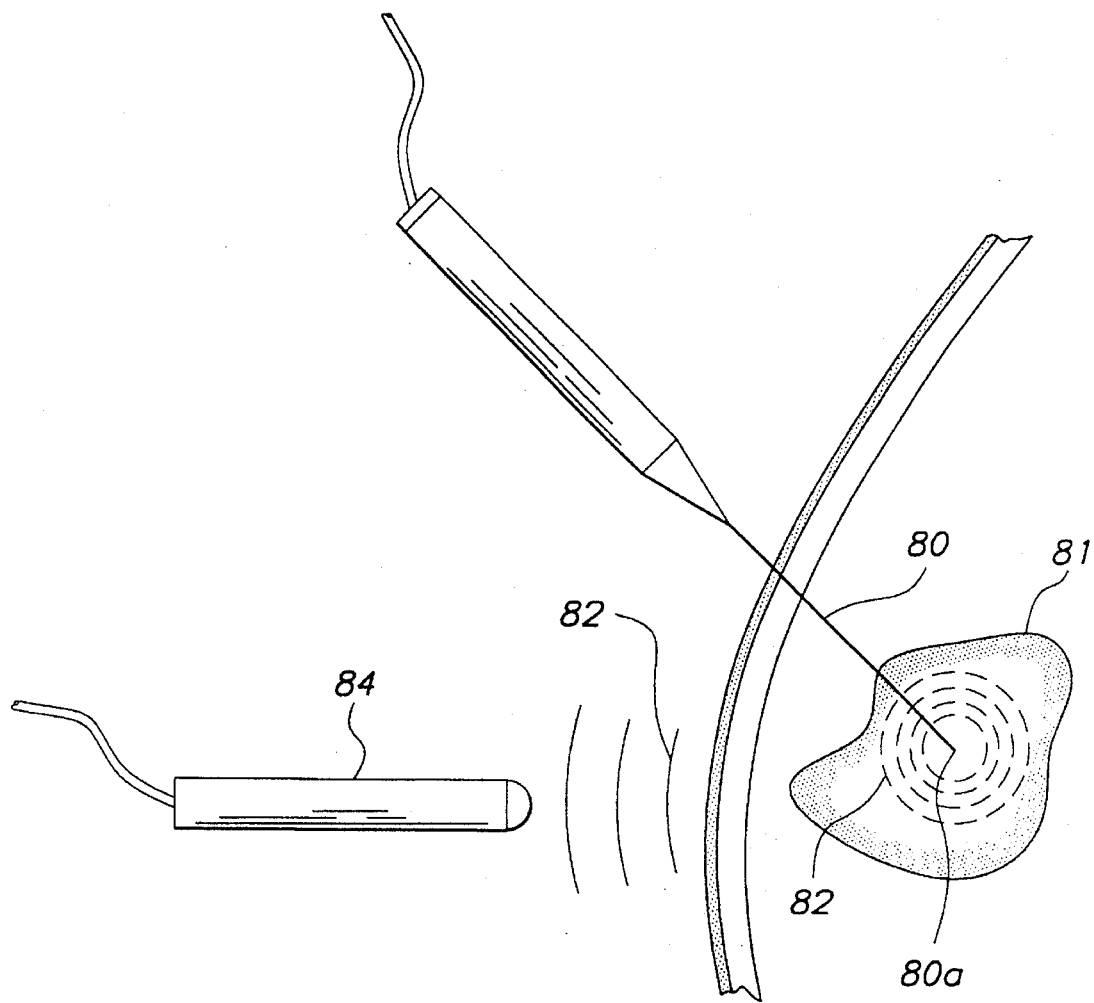
FIG. 4 illustrates a needle light input attachment and light sensor attachment of the present invention.

A more preferred system in accordance with the present invention shown in FIGS. 3 and 4, provides for three dimensional measurements of the oxygen pressure in tissue using a needle phosphorimeter. This embodiment provides for precise measurements of the oxygen pressure in a section of tissue and for the isolation of specific tissue portions.

In this embodiment, a phosphorescent probe (such as the Pd complex of meso tetra-(4-carboxyphenyl) porphone) is injected into the blood of a patient. A light flash system having a frequency of less than 5 µsec half time is used for excitation of the phosphorescent material. In a preferred embodiment, the flash system includes a low voltage power supply 70 which powers a lamp trigger 72 and flash lamp 74. Light from the flash lamp 74 is filtered 76 and reduced so as to propagate along a 0.2 mm fiber light guide 78. The distal end of the light guide 78 is encased within a needle 80. The light guide extends axially through the needle 80. The needle 80 can be inserted into body tissue or a body portion 81 in a manner analogous to that of microdialysis probes.

The excitation light emitted from the distal end 80a of the needle 80 is scattered by the tissue and absorbed. Upon exciting the phosphorescent probe, the excitation light causes the emission of phosphorescent light having a radius of visibility 82. Referring to FIG. 3, the radius 82 of the illuminated volume of tissue (the sample tissue volume) may be adjusted by altering the wavelengths of the excitation light. The radius will be between about 50 to 100 µm when the excitation light has a wavelength of 415 nm, and between about 0.5 to 1 mm when the excitation light has a wavelength of 530 mm The emitted light signal, which has a wavelength greater than about 650 nm is not significantly absorbed by the tissue and is randomly scattered through the tissue. The phosphorescence emission is then collected by a collector lens system 84 placed near the tissue surface. The collected emission is filtered 86 and the signal conducted to a photomultiplier 88 for detection. The resulting signal is amplified 90 and the phosphorescence decay curve determined. In a preferred embodiment, the signal is digitized with, for example, a 12 bit, 1 MHz A/D board 92, and then analyzed with a microcomputer 94.

Because the phosphorescence is emitted only from the volume of tissue which is exposed to the excitation light at the end of the needle 80, the phosphorescence lifetime is an accurate measure of the oxygen pressure in the blood for that volume of tissue.

The system of this embodiment may utilize data handling and analysis including deconvolution routines for determining the fit of the decay to a single or multiple exponentials. In a uniform environment, the decay of the oxygen is a single exponential, thereby allowing quantitative calculation of the oxygen pressure in the immediate environment of the needle tip. With the method and apparatus of the embodiment of FIGS. 3 and 4, it is possible to make rapid repetitive measurements of phosphorescence lifetime (to at least 20 times per second), thereby providing excellent temporal and spatial resolution of the changes in oxygen pressure.

The distribution of the oxygen in the tissue may be determined by attaching the needle 80 to a holder device which allows precise orientation and controlled depth of insertion into the tissue. As the needle 80 is inserted, the phosphorimeter is used to continuously measure the phosphorescence lifetime. A graph can then be made of the oxygen pressure verses depth or spatial orientation in the tissue.

The insertion of the needle at multiple places in the tissue provides for the generation of a three dimensional map of the oxygen pressure. It is to be appreciated that variations in the intensity of the measured phosphorescence with respect to position or depth in the tissue, does not affect the oxygen measurement, as the phosphorescence lifetime is independent of this parameter, as discussed in U.S. Pat. No. 4,947,850.

The embodiment of FIGS. 3 and 4 thus utilizes three properties of the phosphorescence method which make it superior to existing technology, such as the use of micro-oxygen electrodes. Initially, the excitation light for some of phosphorescent probes is preferably within the wavelength range of 400 to 600 nm. Within this wavelength range, the tissue absorption varies from very strong in the blue region (400 to 450 nm) and gradually progresses to weak absorption in the red region. Throughout this wavelength range, the tissue absorbance determines the distance from the needle that will be illuminated by the flash of the excitation light. The measured phosphorescence must originate from the illuminated section of tissue sampled to be varied from about 100 um to greater than 1 m, subject to the choice of the operator. Oxygen electrodes, in contrast, sample only oxygen diffusing to the electrode tip, maximizing the effects of tissue damage on the measurements.

Second, the emitted phosphorescence is in the near infrared region of the spectrum, having a wavelength of from about 630 to 950 nanometers. Tissue absorption is very weak at this wavelength. Thus, the phosphorescence emitted from the illuminated region near the tip of the needle is scattered but not absorbed. The emitted phosphorescence can travel long distances through the tissue to the surface where it leaves the tissue and can be collected by the collector. Only the excitation light need be transmitted through the needle, and the phosphorescence can be collected with high efficiency using a large collector lens.

Finally, the emission of the phosphorescence through the tissue does not influence the measured phosphorescence lifetime, because this interval is very short compared to the decay of the phosphorescence.

The present invention has been described in accordance with the above detailed preferred embodiment. It is to be appreciated that other embodiments may fulfill the spirit of the present invention and that the true nature and scope of the present invention is to be determined with reference to the claims appended hereto.

What is claimed is:

1. A method for producing a phosphorescent emission within a body portion which may be detected externally to the body portion comprising the following steps:

inserting a phosphorescent probe material into the body portion;

inserting a needle into said body portion, said needle encasing a light guide propagating a light signal having a first wavelength through said light guide and into said body portion, said light signal exciting said phosphorescent probe material within said body portion, and producing an emission of phosphorescent light having a radius of visibility which can be detected at a surface of said body; and collecting said emitted phosphorescent light at the surface of said body.

2. The method of claim 1 wherein said step of propagating includes generating said propagated light signal by a flash lamp operating at a frequency of less than about 10 μsec.

3. The method of claim 2 wherein further including the step of altering the radius of visibility of the phosphorescent light emission by propagating a second signal having a second wavelength.

4. The method of claim 1 wherein said radius of visibility is about 50 to 100 μm when said propagated light signal has a wavelength of about 415 nanometers.

5. The method of claim 1 wherein said radius of visibility is between about 0.5 to 1 mm when said propagated light signal has a wavelength of about 530 nanometers.

6. A method for producing a phosphorescent emission from a body portion comprising the following steps:

inserting phosphorescent material into the body portion having a surface;

inserting a needle into said body portion, said needle encasing a light guide which extends axially through said needle, propagating a signal through said light guide through said needle, said light signal exciting said phosphorescent material within said body portion, to produce the emission of a phosphorescent light signal having a radius of emission; and collecting said phosphorescent emission using a collector system placed proximate to the surface of said body portion and determining the oxygen pressure of said body portion.

7. A method for determining an oxygen pressure of a body portion having an interior region and a surface portion comprising the following steps:

inserting phosphorescent material into interior region of the body portion;

inserting a needle into said interior region of said body portion, said needle encasing a light guide extending axially through said needle;

propagating a light signal through said light guide and into said body portion, said light signal exciting said phosphorescent material within said interior region of said body portion, to produce the emission of a phosphorescent light signal having a radius of emission within said interior, said emission having a duration being proportional to the oxygen pressure of said interior of said body portion; and collecting said phosphorescent emission using a collector system placed proximate to the surface portion of said body portion, calculating the oxygen pressure of the body portion based upon the collected phosphorescent emission.

8. A method for determining the oxygen pressure of at least two points of a body having an interior and a surface portion comprising the following steps:

inserting phosphorescent material into the interior of the body portion;

inserting a needle into said interior of the body portion at a first point of said body portion, said needle encasing a light guide extending axially therethrough;

propagating a light signal through said light guide and into said interior of said body portion at said first point, said light signal exciting said phosphorescent material within said interior of said body portion at said first point, thus producing a first emission of a phosphorescent light signal having a radius of emission, the duration of said emission being proportional to the oxygen pressure at said first point;

collecting said first phosphorescent emission using a collector lens placed proximate to the surface of said body portion;

moving said needle to a second point within said body portion;

propagating a light signal through said light guide and into said body portion at said second point, said light signal exciting said phosphorescent material within said body portion, at said second point, thus producing the emission of a second phosphorescent light signal, the duration of said emission being proportional to the oxygen pressure at said second point; and collecting said second phosphorescent emission using a collector lens placed proximate to the surface of said body portion.

9. The method of claim 8 further comprising the additional step of plotting the collected first and second phosphorescent emissions on a graph.

10. Apparatus for determining an oxygen pressure of a body portion having a surface and an interior portion, and an oxygen pressure and containing a phosphorescent material comprising:

a needle, having an axial passageway, for insertion into the interior of said body portion containing a phosphorescent medium;

means for generating an excitation light signal;, a light guide having a first end connected to said excitation light means, and a second end extending through said axial passageway, said light guide transmitting an excitation light signal into said interior body portion so as excite said phosphorescent material within said body portion thereby producing an emission of phosphorescent light, said emission having a duration being proportional to the oxygen pressure of said body portion; and means proximate to the outside surface of said body portion for collecting said phosphorescent emission means for calculating the oxygen pressure of the body portion based upon the collected phosphorescent emission.

* * * * *